(12) United States Patent
Woehr et al.

(10) Patent No.: US 9,114,231 B2
(45) Date of Patent: Aug. 25, 2015

(54) VALVED CATHETER ASSEMBLIES AND RELATED METHODS

(71) Applicant: B. BRAUN MELSUNGEN AG, Melsungen (DE)

(72) Inventors: Kevin Woehr, Felsberg (DE); Edwin L. Burnard, Fogelsville, PA (US)

(73) Assignee: B. Braun Melsungen AG, Melsungen (DE)

( * ) Notice: Subject to any disclaimer, the term of this patent is extended or adjusted under 35 U.S.C. 154(b) by 0 days.

(21) Appl. No.: 14/012,568

(22) Filed: Aug. 28, 2013

(65) Prior Publication Data

US 2014/0276434 A1    Sep. 18, 2014

Related U.S. Application Data

(60) Provisional application No. 61/799,286, filed on Mar. 15, 2013.

(51) Int. Cl.
*A61M 25/00* (2006.01)
*A61M 25/06* (2006.01)
*A61M 39/06* (2006.01)
(Continued)

(52) U.S. Cl.
CPC ........ *A61M 25/0075* (2013.01); *A61M 25/0606* (2013.01); *A61M 25/0618* (2013.01); *A61M 39/0606* (2013.01); *A61M 39/0693* (2013.01); *A61M 39/24* (2013.01); *A61M 39/26* (2013.01); *A61M 2039/062* (2013.01); *A61M 2039/064* (2013.01); *A61M 2039/0653* (2013.01)

(58) Field of Classification Search
CPC ............. A61B 17/3498; A61M 39/24; A61M 39/045; A61M 2039/0633; A61M 2039/064; A61M 2039/0666; A61M 2039/2426; A61M 2039/2433; A61M 2039/244
USPC .......... 604/167.01–167.04, 168.01, 244, 247, 604/256, 264; 137/601.2, 849; 251/149.1
See application file for complete search history.

(56) References Cited

U.S. PATENT DOCUMENTS 4,673,393 A  *  6/1987  Suzuki et al. ............ 604/167.04
5,114,408 A  *  5/1992  Fleischhaker et al. ... 604/167.04
6,352,520 B1 *  3/2002  Miyazaki ................. 604/167.03
(Continued)

FOREIGN PATENT DOCUMENTS

EP    0875262    11/1998
EP    2213328    8/2010
FR    2829396    3/2003

OTHER PUBLICATIONS

International Search Report on related PCT Application No. PCT/EP2014/055089 from International Searching Authority (EPO) dated Jul. 17, 2014.
(Continued)

*Primary Examiner* — Theodore Stigell
*Assistant Examiner* — Amber Stiles
(74) *Attorney, Agent, or Firm* — Klein, O'Neill & Singh, LLP (57) ABSTRACT

Catheter assemblies are described having a catheter hub with a catheter tube and a needle hub with a needle projecting through the catheter tube. The catheter hub has a valve or a septum for stopping or slowing down the flow of fluid in or out of the catheter hub when the valve or septum is closed. The valve has features formed thereon to facilitate venting, opening, closing, or combinations thereof.

25 Claims, 10 Drawing Sheets

(51) Int. Cl.
*A61M 39/24* (2006.01)
*A61M 39/26* (2006.01)

(56) References Cited

U.S. PATENT DOCUMENTS

2001/0053895 A1   12/2001   Vaillancourt
2004/0210194 A1   10/2004   Bonnette et al.
2008/0108944 A1*  5/2008    Woehr et al. ............. 604/164.08
2008/0108976 A1   5/2008    Johnson et al.
2011/0282286 A1   11/2011   Argentine

OTHER PUBLICATIONS

Written Opinion on related PCT Application No. PCT/EP2014/055089 from International Searching Authority (EPO) dated Jul. 17, 2014.

* cited by examiner

VALVED CATHETER ASSEMBLIES AND RELATED METHODS

CROSS-REFERENCE TO RELATED APPLICATION(S)

This application claims the benefit of U.S. provisional Application No. 61/799,286, filed Mar. 15, 2013, the contents of which are hereby expressly incorporated herein by reference for all purposes.

FIELD OF ART

The current system, device, and method relate to infusion devices, and specifically to intravenous ("IV") catheters. In particular, the system, device, and method relate to a flushable peripheral intravenous catheter assembly having features to enable selective activation of fluid flow through the catheter assembly.

BACKGROUND

Catheters are commonly used for a variety of infusion therapies. For example, catheters are used for infusing fluids, such as normal saline solution, various medicaments, and total parenteral nutrition, into a patient, withdrawing blood from a patient, or monitoring various parameters of the patient's vascular system.

Catheters and/or needles are typically coupled to a catheter adapter to enable attachment of IV tubing to the catheter. Thus, following placement of the catheter or needle into the vasculature of a patient, the catheter adapter is coupled to a fluid source via a section of IV tubing. In order to verify proper placement of the needle and/or catheter in the blood vessel, the clinician generally confirms that there is "flashback" of blood in a flashback chamber of the catheter assembly.

Once proper placement of the catheter is confirmed, the clinician must then attach the catheter adapter to a section of IV tubing, or continue to manually occlude the vein to prevent undesirable exposure to blood. The process of coupling the catheter adapter to the section of IV tubing requires the clinician to awkwardly maintain pressure on the vein of the patient while simultaneously coupling the catheter adapter and the IV tubing. A common, yet undesirable practice is to permit blood to temporarily and freely flow from the catheter adapter while the clinician locates and couples the IV tubing to the catheter adapter. Another common practice is to attach the catheter adapter to the IV tubing prior to placing the needle or catheter into the vein of the patient. While this method may prevent undesirable exposure to blood, positive pressure within the IV line may also prevent desirable flashback.

Some catheter assemblies further utilize a septum actuator and a split septum, wherein the septum actuator is mechanically advanced through a slit of the septum to provide a fluid pathway through the septum. However, once advanced through the septum, the septum actuator becomes lodged within the slit of the septum and is unable to return to its initial position. As such, the fluid pathway remains in an opened position thereby enabling uncontrolled flow of fluids through the septum.

SUMMARY

Features of the present disclosure generally relate to an IV catheter assembly having a valve for obstructing or restricting fluid flow through the catheter. A valve opener is disposed in the catheter to open the valve. A needle guard for covering the needle tip following successful venipuncture may be incorporated. To facilitate use, the present disclosure further includes features on the valve to facilitate venting, opening of the flaps, closing of the flaps, or combinations thereof.

An exemplary feature of the present disclosure includes a catheter assembly comprising a catheter hub comprising an interior cavity, an opening at a proximal end, and a catheter tube attached thereto and extending from a distal end and a needle having a needle shaft defining a needle axis projecting distally of an end of a needle hub, said needle projecting through the catheter tube and comprising a needle tip. A valve sized and shaped to obstruct fluid flow can be positioned inside the interior cavity of the catheter hub and in contact with the interior cavity, said valve comprising a valve perimeter surrounding a wall surface comprising a thickness, at least one slit defining at least two flaps, and a void having a void perimeter inwardly positioned relative to the valve perimeter and formed through only part of the thickness of the wall surface. A valve opening device is slidingly disposed in the catheter hub to actuate the valve, the valve opening device comprising a nose section having a tapered end for pushing the valve to open the slit of the valve and a plunger end having a plunger element extending proximally of the nose section; the plunger element being sufficiently rigid to transfer a distally directed force to the nose section to push the valve to open the slit.

The catheter assembly wherein the void has a tapered wall surface.

The catheter assembly wherein the void can have a blunt tip or a sharp tip.

The catheter assembly wherein the valve can further comprise a second void formed through part of the thickness on the wall surface opposite the void.

The catheter assembly wherein the valve can further comprise a plurality of reinforcing ribs located, at least in part, on the flaps.

The catheter assembly can further comprise a needle protective device spaced from the needle tip in a ready position and movable relative to the needle tip to a protective position, at least in part, distally of the needle tip to prevent unintended needle sticks.

The catheter assembly can further comprise a plurality of spaced apart vents cut through the valve perimeter.

Another feature of the present disclosure include a catheter assembly comprising a first hub comprising an interior cavity having a shoulder, a perimeter defining an opening at a proximal end, and a catheter tube having a distal end opening extending distally of the first hub and a needle having a needle shaft defining a needle axis projecting distally of an end of a second hub, said needle projecting through the catheter tube and comprising a needle tip. A valve sized and shaped to obstruct fluid flow comprising a valve body comprising an outer periphery can be positioned inside the catheter hub, said outer periphery comprising at least one vent and said valve body comprising at least one inner slit remote from said outer periphery. A valve opening device can be placed slidingly in the first hub to actuate the valve, the valve opening device comprising a nose section having a tapered end with an opening structured to push the valve to open the plurality of slits and at least one plunger element extending proximally of the nose section and slidable distally when a male implement projects into the opening of the first hub to transfer a distally directed force to the nose section to push the valve to open the at least one slit. In a particular example, the valve has at least one void disposed inwardly of the outer periphery.

The catheter assembly can further comprise a needle guard comprising a proximal wall with an opening sized to obstruct a change in profile on the needle.

The catheter assembly wherein the at least one vent can have a lengthwise slit.

The catheter assembly wherein the at least one vent is a V-shaped notch.

The catheter assembly wherein the void has two side tapered surfaces and one tapered end surface.

The catheter assembly can further comprise a second void positioned opposite the void.

The catheter assembly wherein the valve body can comprise a cylinder with an open end.

The catheter assembly wherein the vent can close when the valve is opened by the valve opening device.

A still yet further feature of the present disclosure is a catheter assembly comprising a first hub comprising an interior cavity having a shoulder, a perimeter defining an opening at a proximal end, and a catheter tube having a distal end opening extending distally of the first hub and a needle having a needle shaft defining a needle axis projecting distally of an end of a second hub, said needle projecting through the catheter tube and comprising a needle tip. A valve sized and shaped to obstruct fluid flow comprising a valve body comprising a wall structure comprising a proximal surface, a distal surface, and an outer periphery, said outer periphery comprising at least one vent and said wall structure of the valve body comprising a Y-shaped slit remote from said outer periphery, the Y-shaped slit comprising three flaps and the wall structure comprising reinforcing ribs on the distal surface on at least part of the three flaps; said valve being positioned inside the interior cavity of the first hub and remaining inside the interior cavity when the needle is removed from the catheter tube and the first hub. A valve opening device slidingly disposed in the first hub to actuate the valve to open the Y-shaped slit and a needle protective device positioned proximal of the valve and at least in part around the needle and distal of the proximal end of the second hub in a ready position, the needle protective device movable to prevent unintended needle sticks in a protective position.

The catheter assembly can further comprise at least two spaced apart vents along the outer periphery.

The catheter assembly wherein the at least one vent can be a slit.

The catheter assembly wherein the at least one vent can have a V-shaped notch.

The catheter assembly wherein the wall structure can further comprise a void formed through only part of a thickness of the wall structure.

BRIEF DESCRIPTION OF THE DRAWINGS

These and other features and advantages of the present device, system, and method will become appreciated as the same becomes better understood with reference to the specification, claims and appended drawings wherein:

DETAILED DESCRIPTION

The detailed description set forth below in connection with the appended drawings is intended as a description of the presently preferred embodiments of valved catheter assemblies provided in accordance with aspects of the present device, system, and method and is not intended to represent the only forms in which the present device, system, and method may be constructed or utilized. The description sets forth the features and the steps for constructing and using the embodiments of the present device, system, and method in connection with the illustrated embodiments. It is to be understood, however, that the same or equivalent functions and structures may be accomplished by different embodiments that are also intended to be encompassed within the spirit and scope of the present disclosure. As denoted elsewhere herein, like element numbers are intended to indicate like or similar elements or features.

Figure 1:
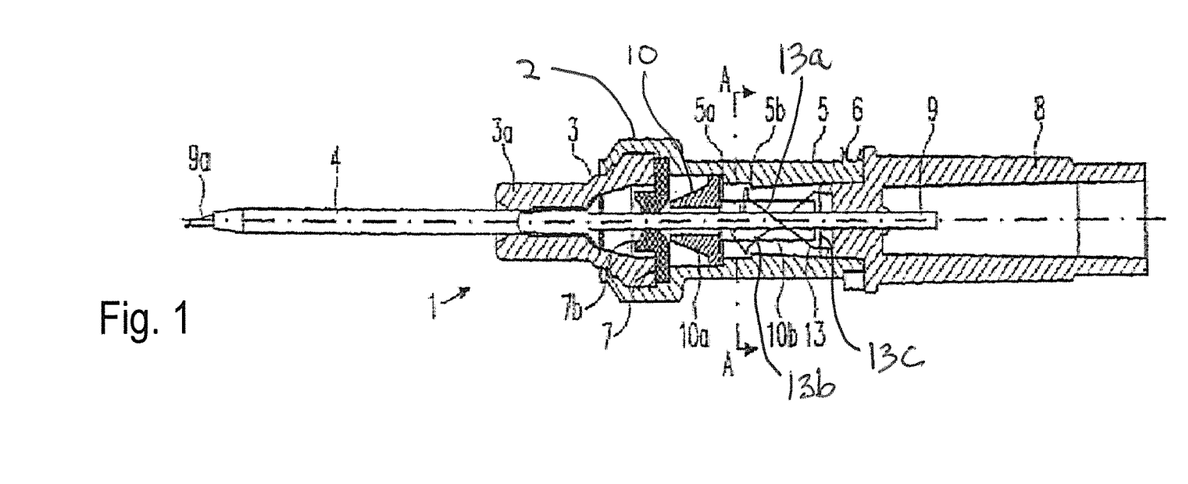
FIG. 1 shows a cross sectional side view of one embodiment of a valved catheter assembly in the ready position.

FIG. 1 shows a valved catheter assembly 1 having a catheter hub 2, which in the embodiment shown has a two-part hub body. A distal hub element or first hub part 3 of the catheter hub has a holding section 3a, such as a nose section, in which a catheter tube 4 is press-fitted. The proximal end of the hub element 3 has an enlarged diameter relative to the distal end portion and forms a connecting section, for example a Luer conical fitting, with a rear hub element or second hub part 5. The distal end of the rear hub part 5 overlaps the proximal end of the front or first hub part 3 and which is provided at its proximal end with a Luer thread 6. Between the two hub parts 3 and 5, a valve 7 in the form of a check valve shaped as a cylinder or disk is inserted and is fixed in place by the two hub elements 3 and 5. In other embodiments, the valve 7 is held in place by securing the valve to the shoulder on hub element 3 using adhesives or welding while omitting the shoulder of hub element 5. In still yet other examples, a single catheter hub body is used with internal shoulders or undercuts incorporated for retaining the valve 7 therein. In still another embodiment of the present disclosure, the valve is held in the catheter hub by an interference fit.

Figure 2:
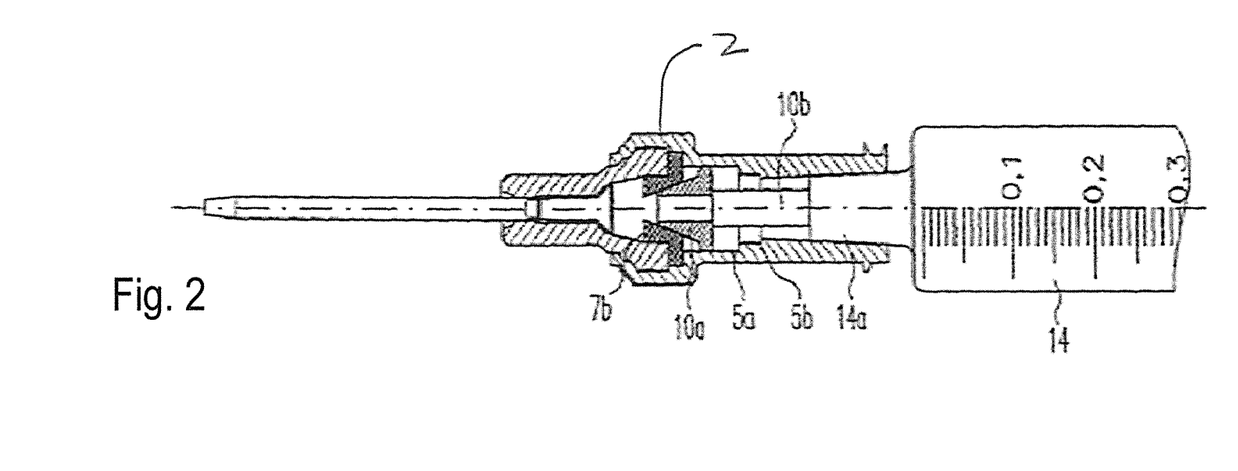
FIG. 2 shows a cross sectional side view of the embodiment of FIG. 1 in the activated position.

In the ready position of FIG. 1, a nose section of a needle hub 8 is inserted into the catheter hub 2. A hollow needle 9 is fixed to the nose section and extends through the valve 7, the catheter hub 2, and the catheter tube 4 so that the needle tip 9a is exposed beyond the tapered end of the catheter tube 4. Between needle hub 8 and the valve 7 and inside the catheter hub 2, a valve opening device or valve actuator 10 with a truncated cone-shaped locating section or tapered nose end 10a for opening the valve 7 is slidably or displaceably arranged, as shown in FIG. 2. On the proximal side of the valve actuator 10, a plunger section or pusher end 10b is provided for being pushed by the male Luer conical fitting of a medical implement, such a syringe tip or an IV tubing adaptor, to open the valve. The pusher end 10b adjoins the tapered nose end 10a. In an example, the tapered nose section 10a incorporates a groove to facilitate engagement with the valve so that even if the medical implement no longer pushes on the valve actuator 10, the tapered nose and remains engaged with the valve. This is depicted as the grooved section 210b of the valve actuator head 210 in FIG. 3. As explained above, a typical exchange of elements could be the use of valve opener 210 in the embodiment of FIGS. 1 and 2. In one example, there is only a single element or leg forming the pusher end. In another example, two legs with a hollow space therebetween are provided. The two proximal ends of the two legs provide a surface to be pushed by the medical implement. The space between the two legs is configured to receive a needle guard element 13. Said differently, the needle guard element 13 is positioned in the space between the two legs. In other examples, a third housing having a cavity is positioned between the catheter hub 2 and the needle of 8. The needle guard element 13 may be positioned in the cavity of the third housing and the third housing having mechanical features to engage the catheter hub and the needle hub. In some examples, the needle guard is omitted and the catheter assemblies only incorporate a valve and a valve opener.

On withdrawal of the hollow needle 9 from the catheter hub 2 following successful venipuncture, a change in profile provided near the needle tip 9a and having the form of a radial projection on the hollow needle which can be formed by light crimping, engages with the outer circumference of a bore in the rear wall 13c of the needle guard 13 so that the needle guard 13 is removed from the catheter hub with the needle 9. Simultaneously, the arms 13a and 13b of the needle guard cover the needle tip to prevent needle sticks. In other examples, the change in profile can include a sleeve, a notch, or a material buildup on the shaft of the needle. In this separated position, the valve 7, due to its elasticity, closes the through-hole for the hollow needle 9 so that no blood can flow out through the catheter 4. As further discussed below with reference to FIGS. 6 and 7, valves provided herein can include three slits 54 starting from the middle of the valve and extending radially over a short radial distance towards the outer perimeter to form elastic flaps that can be expanded by the hollow needle and closed when the needle is removed. In some examples, the flaps remain open and engaged with a valve opener.

FIG. 2 shows the insertion of a syringe 14 in the catheter hub 2 to either inject a fluid, such as medicament, through the catheter hub or draw a sample of a bodily fluid like blood. As shown, the syringe tip 14a of the syringe 14 abuts the pusher end 10b of the valve actuating element 10 and pushes it against the valve 7 so that the tapered nose section 10a opens the slits 7a thereby opening the valve so that liquid can flow there-across.

As shown, the nose end 10a of the actuator 10 is inclined. Thus, as the syringe is removed and the forward force on the actuator is removed, the elasticity of the material of the valve 7 is sufficient for the three slits 7a to uncoil and push the actuator in the proximal direction to close the seal 7. The valve 7 therefore automatically closes upon withdraw of the pushing force on the actuator.

A shoulder 5a is shown in the rear hub element 5 in FIGS. 1 and 2. The shoulder 5a acts as a stop for the actuator 10 when the flange on the actuator abuts the shoulder, which defines the proximal most position of the actuator. In other examples, the second hub section may incorporate other structural features, such as a tapered internal cavity, to stop the proximal travel of the actuator.

Also shown in the inner circumference of the bore of the hub element 5 is a second shoulder 5b just proximal of the first shoulder 5a. The two radially outer areas of the spring arms of the needle guard are configured to abut the second shoulder 5b in the ready position in FIG. 1. When the needle hub 8 with the hollow needle 9 is removed from the catheter hub 2, the needle guard 13 is held generally stationary by the shoulder 5b until the change in profile, such as a crimp, near the needle comes to abut on the rear wall of the needle guard and the needle tip moves proximally of the two distal walls on the needle guard 13. At this point, the two spring arms spring inwards to cover the needle tip and separate from the second shoulder 5b, whereupon the needle guard 13 with the hollow needle 9 can be removed from the catheter hub. Further information regarding the needle guard 13 is discussed in U.S. Pat. No. 7,736,339, the contents of which are expressly incorporated herein by reference.

In the embodiment according to FIGS. 1 and 2, the distal end section of the second hub part 5 is shrunk, welded or bonded onto the proximal end section of the first hub part 3 after the actuating element 10 and the valve 7 are inserted in the hub element 5. It is also possible to join the two hub elements 3 and 5 to one another, for example, using threads, interference, or snap-fit. The needle guard 13 may be inserted together with the hollow needle 9 in the bore of the hub element 5 during assembly via the proximal opening of the hub, wherein the radially outer areas of the spring arms snap in at the shoulder 5b under elastic deformation.

Figure 3:
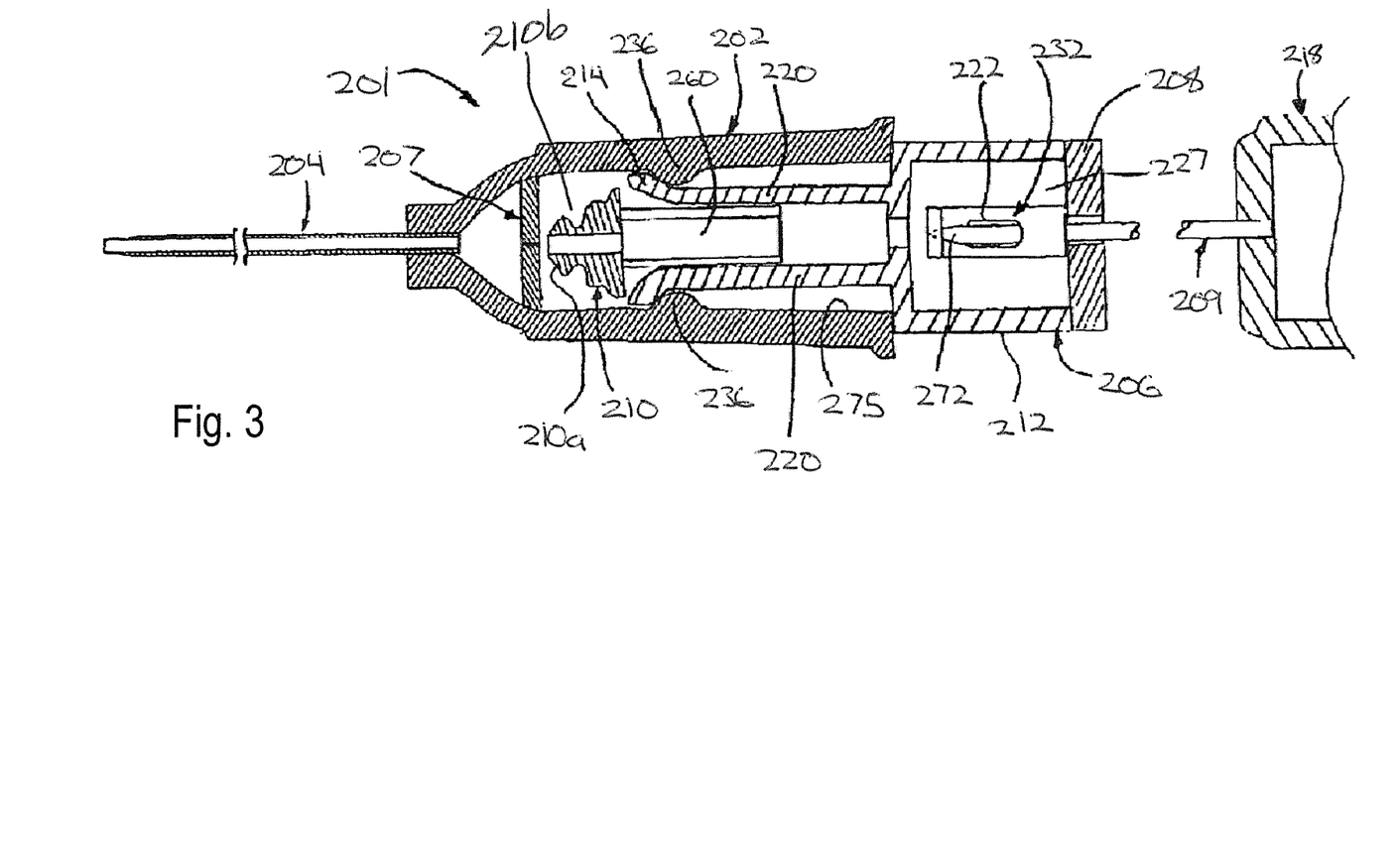
FIG. 3 shows a cross sectional side view of another embodiment of a valved catheter assembly with the needle partially withdrawn.

FIG. 3 is a cross-sectional side view of another embodiment of a valved catheter assembly provided in accordance with aspects of the present system, device, and method, which is generally designated 201. The catheter assembly 201 incorporates similar components as the assembly shown in FIGS. 1 and 2, including a catheter tube 204 attached to a catheter hub 202, a needle 209 attached to a needle hub 218, a valve 207, a valve opening device 210 comprising a tapered distal tip 210a with a grooved section 210b, and a pusher end 260, which in the present embodiment comprises a pair of legs (only one shown) positioned in a bore 275 in the interior of the catheter hub 202.

A tip protector 232 for blocking the needle tip 272 is provided in a third housing 206. In an embodiment, the third housing 206 incorporates a rear plate or panel 208 attached to a housing section 212 for closing an opening 227 on the housing section 212, which has an interior cavity for accommodating the needle guard. The opening 227 on the housing section 212 allows the tip protector 232 to be placed therein during assembly. Thus, while the guard is located inside the third housing, it is also movable relative to the third housing. The rear plate 208 may be attached to the housing section 212 using adhesive, welding, or detents. Alternatively, the housing section 212 may incorporate an opening on a side, orthogonal to the rear plate 208.

In one example, the third housing 206 incorporates a pair of arms 220 each comprising a hook 214. The two hooks 214 are configured to engage the annular bump 236 inside the catheter hub to retain the third housing 206 to the catheter hub 202 in a ready to use position. The two arms 220 are preferably flexible to provide a gripping force against the bump 236, which is higher than the frictional force to withdraw the needle through the tip protector 232, hemostatic valve 207, and catheter 204. Alternatively, the two arms 220 can be biased radially outward to increase the gripping force. Further, the two arms can be biased inwardly against the needle shaft to decrease the gripping force after the needle is withdrawn proximal of the arms 220. Still alternatively, only a single arm is used to attach the third housing to the catheter hub. External structural features are also contemplated for fixing, securing, or attaching the third hub to the catheter hub without projecting the arm into the interior cavity of the catheter hub.

Following successful catheterization, the needle 209 is retracted proximally away from the catheter tube 204 in the same manner as previously discussed. As the needle tip 272 moves proximally of the distal wall of the tip protector 232, the tip protector 232, comprising a needle tip opening 222, engages the needle 209 and further proximal movement of the needle 209 causes the tip protector 232 to pull on the rear plate 208 of the third housing 206, which then disengages the two hooks 214 from the two bumps 236. Thus, the gripping force between the two hooks 214 and the two bumps 236 should be less than the gripping force between the tip protector 232 and the needle 209. In yet other examples, a guard with a proximal wall located inside a third housing is used to engage a change in profile on the needle, similar to the guard of FIG. 1.

Figure 4A:
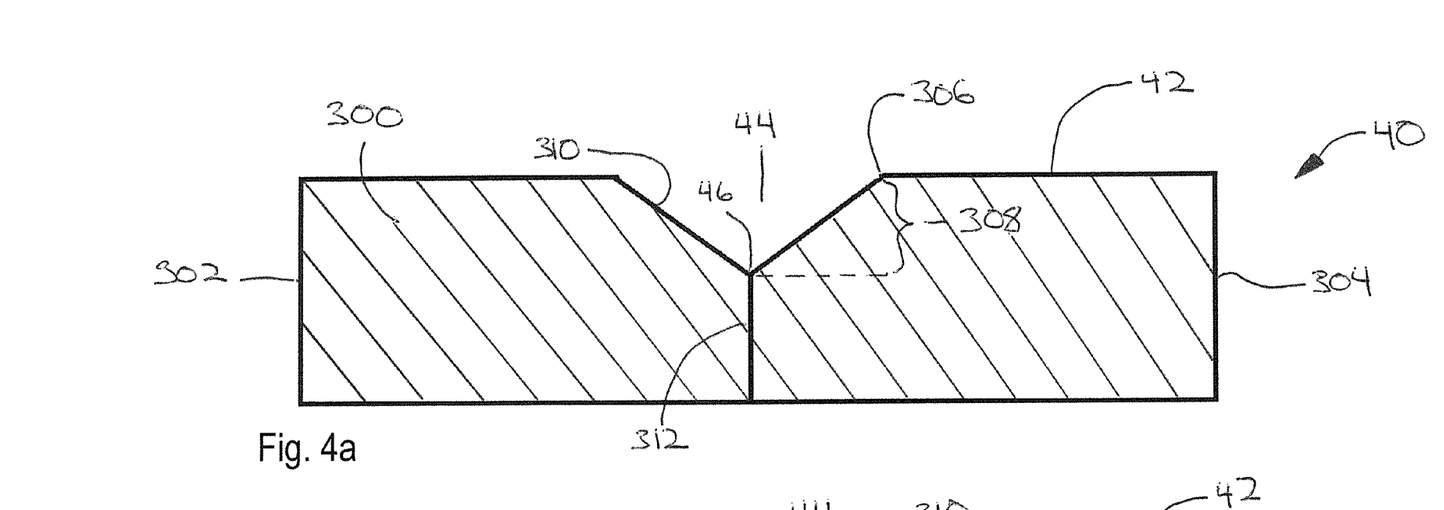
FIG. 4a shows a side view of a valve embodiment with a void on the proximal surface.
Figure 4B:
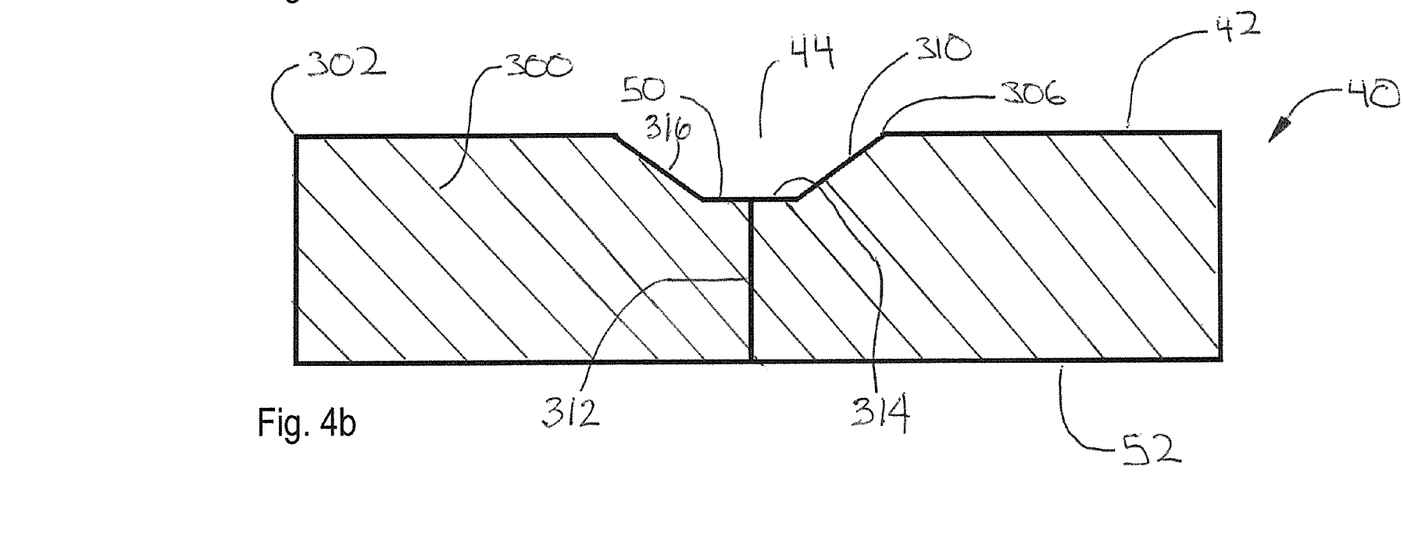
FIG. 4b shows a side view of a valve embodiment with a void on the proximal surface in accordance with another aspect of the present disclosure.

With reference now to FIGS. 4a and 4b, a schematic cross-sectional side view of a first valve 40 embodiment (FIG. 4a) and a second valve embodiment 40 (FIG. 4b) in accordance with aspects of the present disclosure are shown. The valves 40 each comprises a valve body 300 comprising a perimeter 302 and a depth or thickness 304. In one example, the perimeter is round or somewhat oblong. In another example, the perimeter is polygonal. Less preferably, the perimeter has an irregular shape. The valve has a wall structure or body comprising a proximal surface or first surface 42 and a distal surface or second surface 52. The first surface 42 of the two valves 40, both of which resemble a valve disk or disc, is formed or provided with a void 44 partly through the thickness 304 of the disk on the proximal surface at the center thereof. However, the void can be slightly offset or off-center. Each void 44 has a perimeter 306, a wall surface 310, and a depth 308, which depth is about 0.25 to about 0.7 of the total thickness 304 of the valve 40. The perimeter 306 of the void is understood to be recessed or inwardly located from the disk perimeter 302. A through seam 312 is shown representing a mating line between the two or more flaps formed between the centrally formed slits, as further discussed below. In one example (FIG. 4a), the void 44 is formed so that it has a pointed or sharp tip 46. In other embodiment (FIG. 4b), the void may have a flattened or blunted tip 50 along a cross-section. The blunted tip 50 has a base surface 314 that is generally parallel to the first surface 42 and/or the second surface 52 and an inner perimeter 316. Both valves 40 are useable with catheter assemblies, such as the ones shown in FIG. 1 and FIG. 3. The thickness of the valve disk as well as the outside dimension of the disk can vary to accommodate the particular application, such as to fit into different hubs and hubs with only a single hub body versus more than one hub part or body. In other embodiments, the valve disk 40 is located on an end of a cylinder, i.e., a cylinder valve, with the other end of the cylinder being opened.

Figure 5:
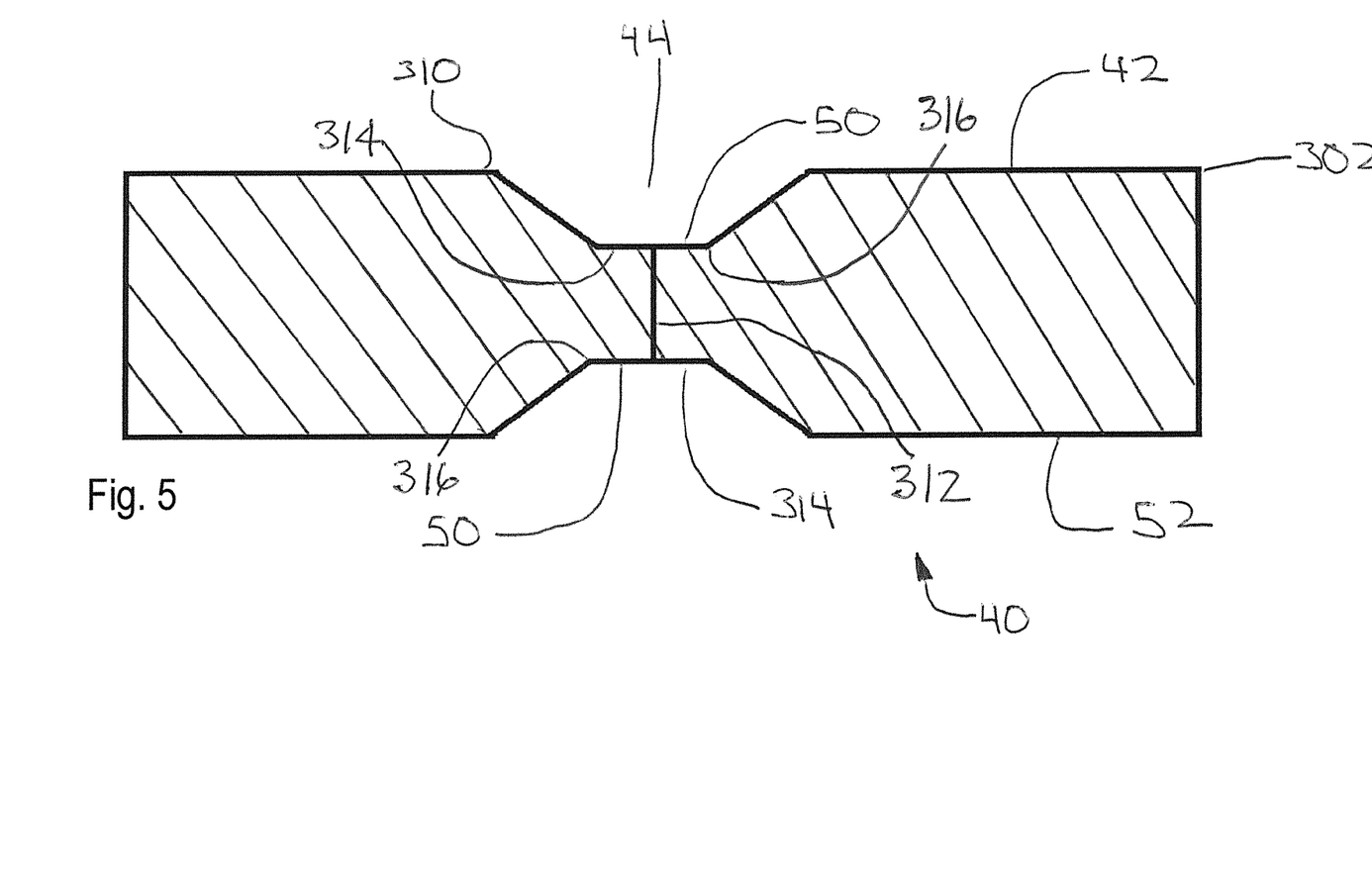
FIG. 5 shows a side view of a valve with two voids on both the proximal and distal surfaces.

FIG. 5 shows a cross-sectional side view of an alternative valve 40 provided in accordance with further aspects of the present disclosure. In the present embodiment, the valve 40 may have blunted 50 or sharp (not shown) tip voids 44 on one or both of the proximal 42 and distal 52 surfaces of the valve. In yet another embodiment, the valve 40 can have a pointed void 46 on one side and a blunted void 50 on another side, similar to a combination of the valve of FIGS. 4a and 4b. Thus, the valve 40 of FIG. 5 may be understood to include two voids with two point tips, two voids with two base surfaces and two perimeters formed around the base surfaces, or two voids with one void having a pointed tip and another void with a base surface with a perimeter formed around the base surface. The valve 40 of FIG. 5 may be useable with the catheter assemblies of FIG. 1 and FIG. 3.

Figures 6, 7:
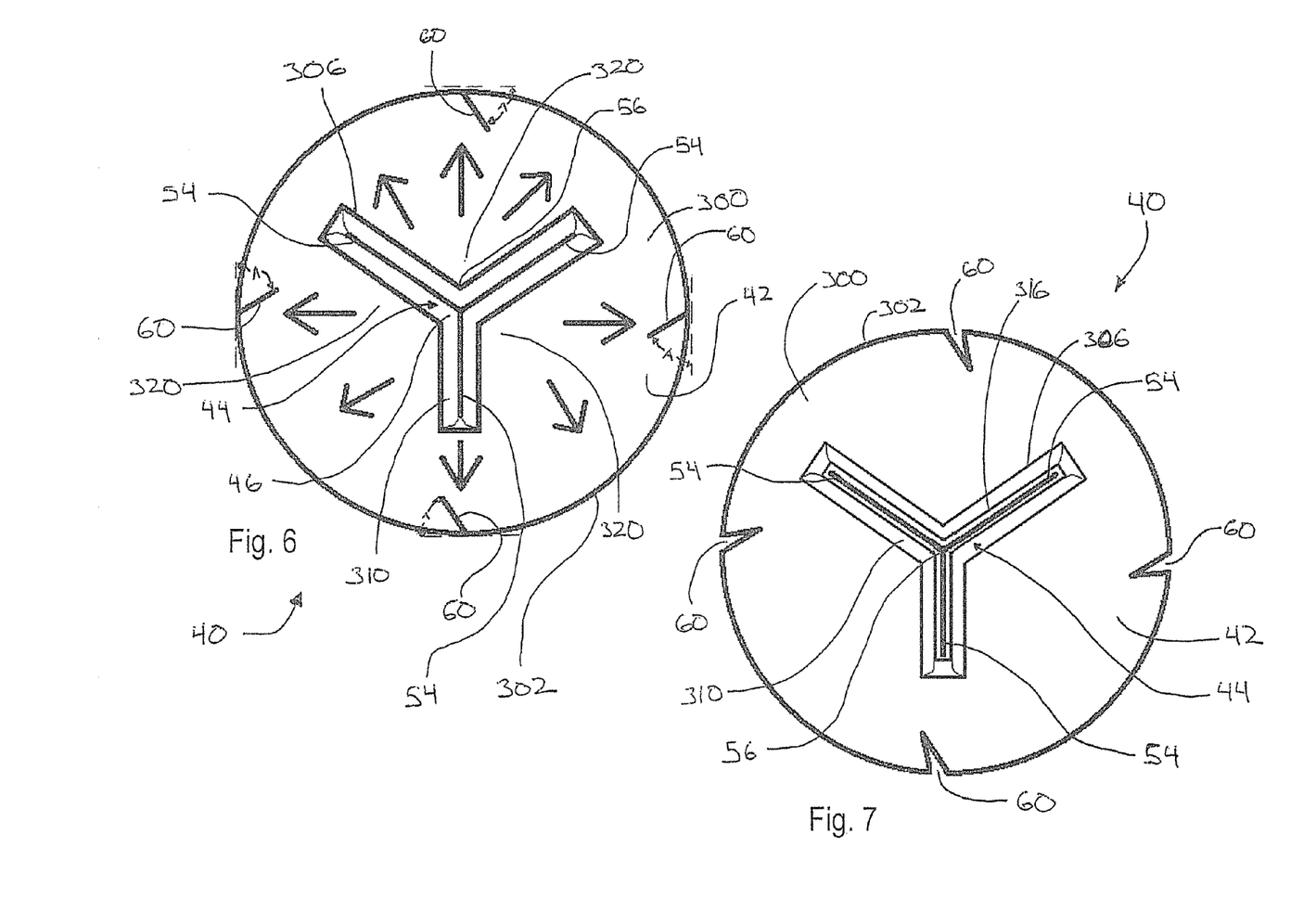
FIG. 6 shows a side view of a valve with a plurality of vents and slits.
FIG. 7 shows a side view of a another valve embodiment with a plurality of vents and slits.

FIGS. 6 and 7 depict two additional valve embodiments. Each of the two valves 40 incorporates three slits 54 that are formed such that one end of each of the three slits join at a common point 56 centrally of the valve. The three slits 54 define three flaps 320 that can flex and un-flex to either open a passage through the valve or close the passage. The flexibility of the flaps, such as their elasticity, can depend on the length of the slits, the material, and the thickness of the valve, among others. From this common point 56, the slits 54 extend radially outward. As shown, the slits extend radially outwardly but not past the inner perimeter 316 of the void 44 with a base surface (FIG. 7) or the void perimeter 306 (FIG. 6), which is located radially inwardly of the disk perimeter 302. The slits are spaced at even intervals of approximately 120 degrees around the common point 56. In other embodiments, the slits can be placed in different intervals around the common point, such as a "T" configuration or in other than 120 degrees intervals. There may also be more than three slits, such as 4 to 6 slits. There may also be only one slit that runs through the center point of the disc forming two flaps. In other words, the single slit can be seen as two slits that meet at the center point of the disc. There can also be a "U" shaped slit that is centered on the same center point as the disc but the slit does not run through the center point. The slits extend through the width or thickness 304 of the valve, from the proximal surface 42 to the distal surface 52 (See, e.g., FIGS. 4a and 4b), including through any portion of a void 44, if one is present. The slits are cut to a length equal to about 0.25 to about 0.7 of the length of the radius of the valve.

In one example, vents 60 are formed on the perimeter 302 of the valve 40. In some embodiments, there are four vents 60, spaced at approximately 90 degree intervals around the perimeter of the valve. Other embodiments contemplate different numbers of vents at different spacing distances or only one vent.

As shown in FIG. 6, the vents 60 are cut inwardly from the circumferential perimeter 302 of the valve 40. The vents 60 are cut at an acute angle "A" measured from a line running tangent to the circumference of the valve. In one example, the acute angle measured from the line running tangent is about 45 degrees but other angles are contemplated, such as 60 degrees and 30 degrees or at some angle in between. In some embodiments, the vents are formed by simple slits or simple cuts through the valve body 300 along or near the circumferential perimeter 302. In other embodiments, the vents 60 are v-shaped notches, such as that shown in FIG. 7. The gap or size of each V-shaped notch is about 10 degree to about 15 degrees, but can be as much as 30 degrees. The cuts for the vents are relatively shallow, extending only about 0.1 to about 0.25 of the length of the radius of the valve from the circumferential perimeter 302 to the termination of each notch of the slit. The vents are configured to permit air to pass from the distal side to the proximal side of the valve following successful venipuncture. While the vents of FIG. 7 appear large and susceptible to the flow of blood there-across, upon opening the slits with the actuator, the outward force on the slits will force the V-shaped vents to close. This closing action is represented by the arrows shown in FIG. 6, which depict a compressive force imparted to the valve 40 when a medical implement is inserted through the valve to open the slits, as further discussed below.

The valves discussed herein may be made from any elastic and flexible or semi-flexible material that is compatible with medical applications, such as being compatible with exposure to blood, medicaments, and other fluids commonly encountered during infusion procedures.

In operation, as shown in FIG. 2, the valve 7, which can be any valve discussed elsewhere herein, is opened by the valve actuator 10. The valve actuator 10 may be displaced or moved by the insertion of a medical implement, such as a male Luer member or a tip of a syringe 14, into the catheter hub 2. In some embodiments, the valve 7 is permanently opened by the insertion of the valve actuator 10. For example, if the tip of the nose end 10a of the actuator 10 is inserted in through the slits sufficiently deep, the slits will remain open even after the syringe has been removed. This more permanent open position can further be facilitated by incorporating a recess or groove 210b on the nose section of the actuator to engage part of the flaps 320 formed by the slits. Conversely, when the actuator 10 merely opens the flaps 320, the flaps are sufficiently resilient and will un-flex to close and move the actuator proximally upon withdraw of the syringe.

With reference again to FIG. 6 and as previously alluded to, when a valve actuator is inserted into the valve, the valve actuator directs a radial outward force on the valve body 300, as indicated by the arrows. The radially outward directed force, indicated by the arrows, causes the valve body 300 to compress radially outwardly against the outer constrain on the valve thus closing in any vent 60 around the perimeter that may be opened. Again, when the valve opener 10 enters the valve 40, it does so by moving from a proximal surface or first surface 42 of the valve towards its distal or second surface 52 away from the proximal opening of the catheter hub (See, e.g., FIGS. 4a and 4b). Because of the proximal to distal movement of the valve opener 10 when it enters the valve 40, the vents 60 will each be caused to progressively close from its proximal side to its distal side, i.e., progressively along its depth starting from its proximal side, as well as progressively from its radial inward most gap and outwardly to its outer most radial gap, at or near the valve perimeter 302. Thus, the vents 60 close progressively from the proximal end of each vent, corresponding with the proximal surface 42 of the valve 40, to the distal end of each vent, corresponding with the distal surface 52 of the valve, and consequently has the effect of squeezing any blood out of the vents 60. The removal of blood by the squeezing action will prevent coagulation in the vents, which will in turn reduce the possibility of infection. It also prevents hemolysis, which would render the blood sample unusable.

With the vents 60 open, the valve, when used in a catheter application, can vent air to allow some flashback. When a greater pressure differential is introduced on the proximal side of the valve, such as when a vacuum vial or tube for collecting blood samples is connected to the catheter hub, or, as shown in FIG. 2, a syringe 14 is connected and the plunger (not shown) withdrawn, blood is drawn toward the valve 7 due to the pressure differential. In the case of the above-described embodiments, the vents 60 are closed automatically upon insertion of the valve opener 10 in order to direct the blood solely through the slit opening and into the syringe or the vacuum vial.

Figure 8:
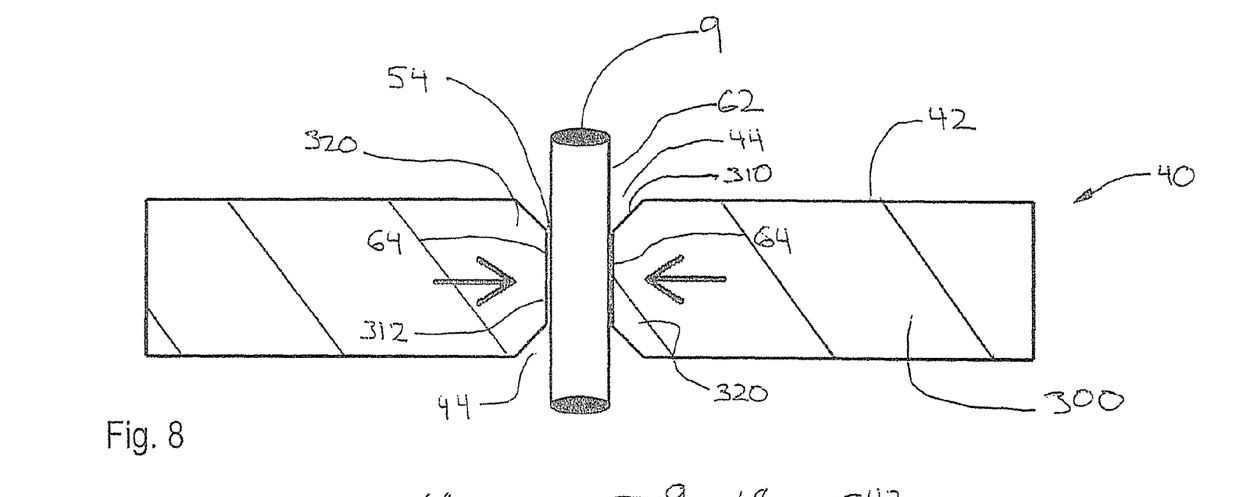
FIG. 8 shows a side view of a valve having a void and a needle passing therethrough.

FIG. 8 is a schematic cross-sectional side view of a valve 40 provided in accordance with aspect of the present disclosure inside a catheter hub (not shown but resembles condition of FIG. 1) with a needle 9 projecting through the through seam 312 and where a plurality of slits 54 forming a plurality of flaps 320 intersect in a ready position. With at least one void 44 incorporated on the proximal side 42 of the valve 40, the straight needle shaft 62 rests against the interior surfaces 64 of the flaps 320 along the through seams 312. The tapered geometry provided by the tapered surface 310 of the void 44 allows the flaps 320 to un-flex without excess materials hanging up against the needle, thus allowing the needle shaft 62 to rest against the interior surfaces 64. In this configuration, the force vector at the seam 312, indicated by the arrows in FIG. 8 and generated by the elasticity of the valve body 300, is more perpendicular relative to the axis of the needle shaft.

Figure 9:
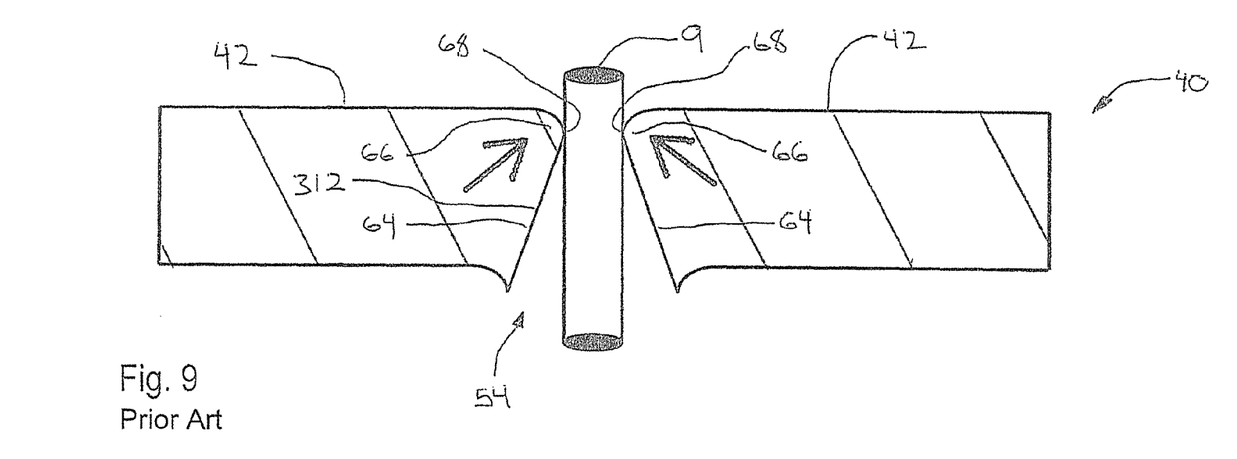
FIG. 9 shows a side view of another a valve without a void and a needle passing therethrough.

As shown in FIG. 9, when the void is omitted from the valve surface, such as when utilizing a standard prior art valve disk with only slits to form flaps but without any void, the force vector, indicated by the arrows, is more proximal or directed to the proximal surface 42. Among other things, this is because the portion of the valve surface 64 that forms the transition 66 from the proximal exterior surface 42 to the seam 312 tends to rotate around the point of contact 68 with the needle 9. Forming the void eliminates this transition 66 and allows the needle 9 to slide more smoothly and readily along the seam and in contact with a larger area of the interior surfaces 64.

Thus when a void or voids 44 are incorporated on the disc surface, then the force of the valve against the needle shaft can be axially neutralized. The void or voids can provide an unexpected solution to the problem of the valve pulling the needle proximally during sterilization of the IV catheter device. Under normal conditions, the axial force on the needle is equalized by the grip on the needle shaft by the tapered tip of the catheter. However, during sterilization with heat and high humidity, certain catheter materials can lessen their grip on the needle shaft and can create a condition that allows the needle to be pulled by the valve. This is an undesirable effect that can lead to the needle bevel being pulled inside the tapered tip of the catheter. This in turn leads to a painful insertion into the patient.

Figures 10, 11:
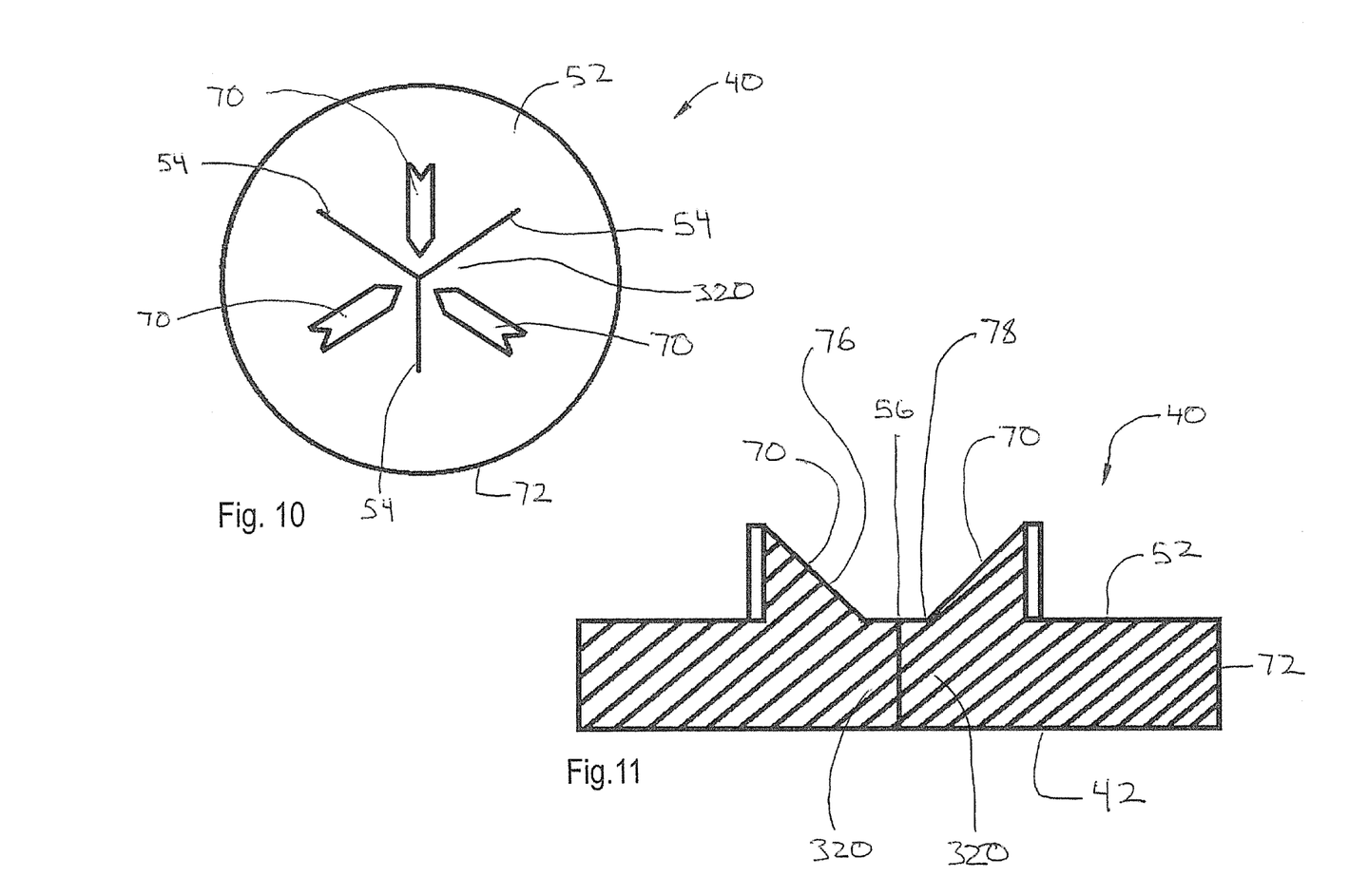
FIG. 10 shows a bottom or end view of one embodiment of a valve with reinforcing ribs on the distal surface.
FIG. 11 shows a cross sectional side view of the valve of FIG. 10 with reinforcing ribs on the distal surface.

FIG. 10 is an end view of yet another valve 40 embodiment in accordance with aspects of the present disclosure and FIG. 11 is a cross-sectional side view thereof. As shown, the valve 40 includes reinforcing ribs 70 on the distal surface 52, which, in the present embodiment, is understood to be the surface or side where the needle comes out. The ribs 70 add to the material thickness of the valve at the flaps and therefore the flaps' rigidity. In some embodiments, the ribs 70 are the same material as the rest of the valve, i.e., a unitarily formed body. In other embodiments, the ribs may be made of the same or a different material and joined to the body of the valve. For example, the ribs may be integrally formed with the valve body, or welded to the valve body after they are formed.

In use, the valve 40 of FIG. 10 opens as normal by a valve opener, such as shown in FIG. 2. Upon removal of the syringe, the ribs 70 will add to the recoil action on the flaps 320 to increase the closing force of the valve to readily push the valve actuator 10 in the proximal direction.

As shown in FIG. 11, the ribs 70 sloped or inclined in the radial outward direction starting from the center 56 of the distal surface 52 to a distally extended position in the direction of the circumferential perimeter 72 of the valve 40. In other embodiments, the slope may be reversed. In some examples, the upper surface 76 of each rib can be straight, concave, convex, or combinations thereof. The starting point 78 of each rib 70 can also start right at the center 56 of the valve rather than being spaced or recessed from the center. In still another example, the proximal surface 42 may incorporate a void 44, similar to that shown in FIG. 4a or 4b. Still furthermore, vents may be incorporated around the outer perimeter, similar to that shown in FIGS. 6 and 7.

Figure 12:
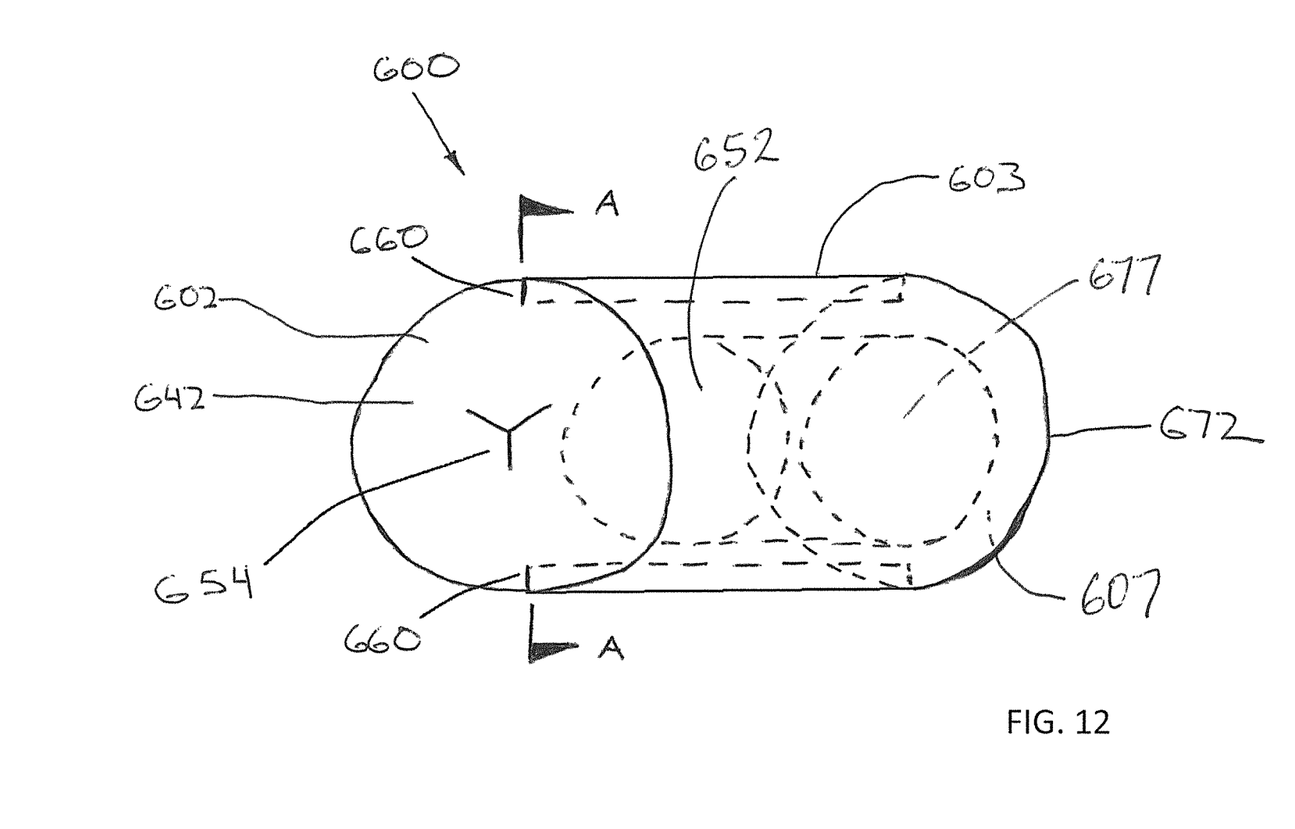
FIG. 12 is a schematic perspective view of yet another valve embodiment provided in accordance with aspects of the present disclosure.

As shown in FIG. 12, the valve 600 may also be embodied as a cylinder. The valve 600 comprises a disk 602 having a first or distal surface 642, a second or proximal surface 652, and a thickness separating the two surfaces, which resembles thickness 304 of FIG. 4a. The disk 602 is positioned at an end of a hollow cylinder section 603 having a length and a body wall thickness defining an interior space and having a hollow or open second end 677. The disk 602 may resemble or incorporate features of any of the above discussed valve disk embodiments with various configurations of valve slits 654 and voids, ribs, and vents. In the present embodiment, vents 660 are incorporated in the hollow cylinder section 603 and run the entire length of the cylinder and are open to the outer perimeter 672 of the cylinder. The vent paths can be straight or curved. The valve 600 may be used with many catheter assemblies by simply sliding the valve into the interior cavity of a catheter hub with the disk surface 652 facing the proximal opening of the catheter hub. A stepped pin tool can be used to push the valve into the catheter hub. The smaller tip of the pin tool can enter the cylindrical portion 603 of the valve to push the proximal surface 652 and the larger step diameter portion can push against the proximal end surface 607 of the cylinder portion 603 to locate the valve 600 inside the catheter hub.

Figures 13, 14:
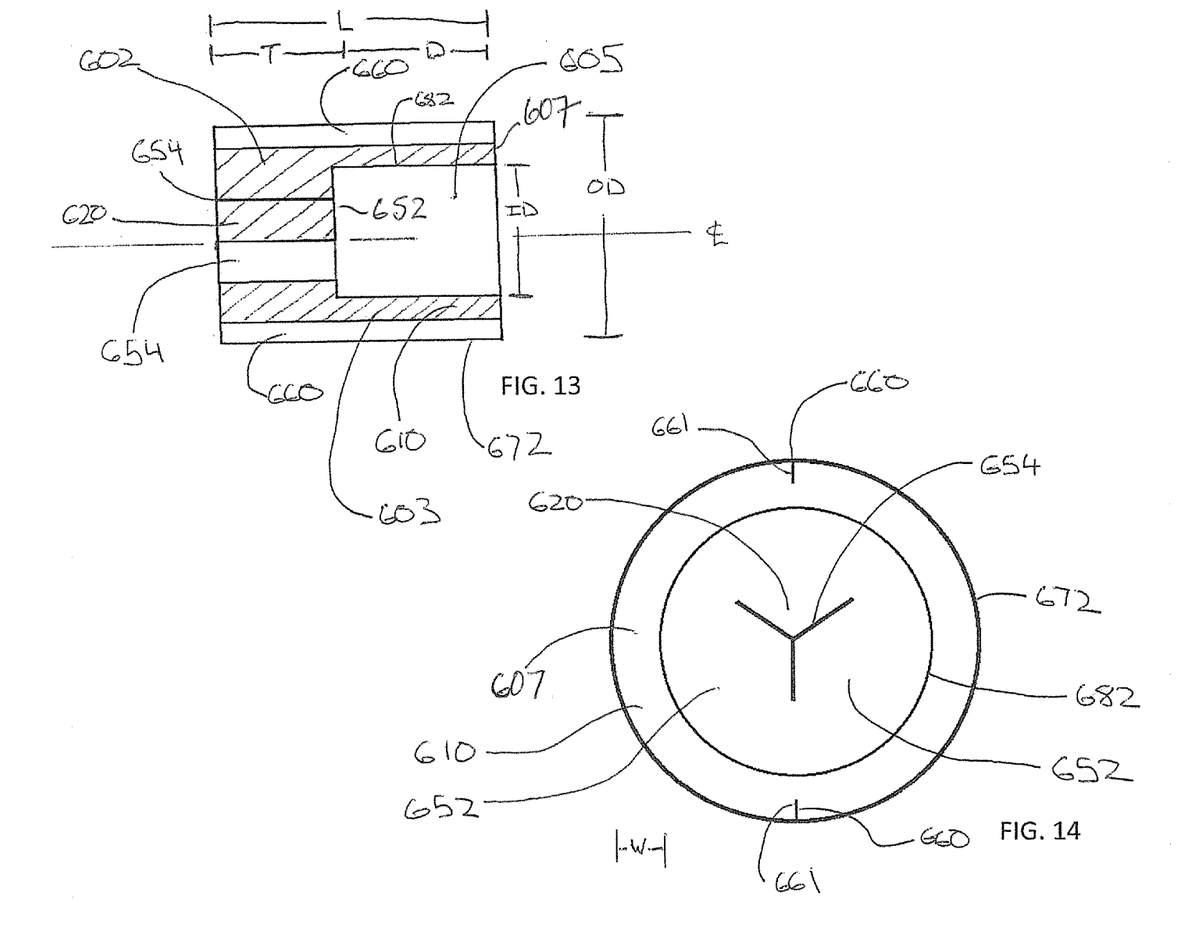
FIG. 13 is a cross-sectional side view of the valve of FIG. 12 sectioned along lines A-A.
FIG. 14 is an end view of the valve of FIG. 12 taken from the end opposite the surface with the slits.

As shown in FIG. 13, the hollow cylinder section 603 has an outer diameter OD and an inner diameter ID defining a bore 605. In some embodiments, the interior walls 682 of the bore 605 are smooth. In other embodiments, the interior walls 682 are textured. In some embodiments, the wall 610 of the cylinder is of uniform thickness around the perimeter 672, except for the vent locations. In other embodiments, the wall 610 can be formed with varying thicknesses, which define the shape of the bore 605. The vents 660 are cut to a depth of about half the thickness of the cylinder wall 610. The slits 654 and the corresponding flaps 620 pass through the thickness of the valve disk section 602 and open into the hollow cylinder section 603.

As shown in FIG. 14, the hollow cylinder wall 610 defines a proximal end face 607. As discussed above, the slits 654 and the corresponding flaps 620 pass through the thickness of the valve disk and are visible from the proximal end. Likewise, the vents 660 run the length L of the valve and the proximal end of the vent 661 is visible.

Figure 15:
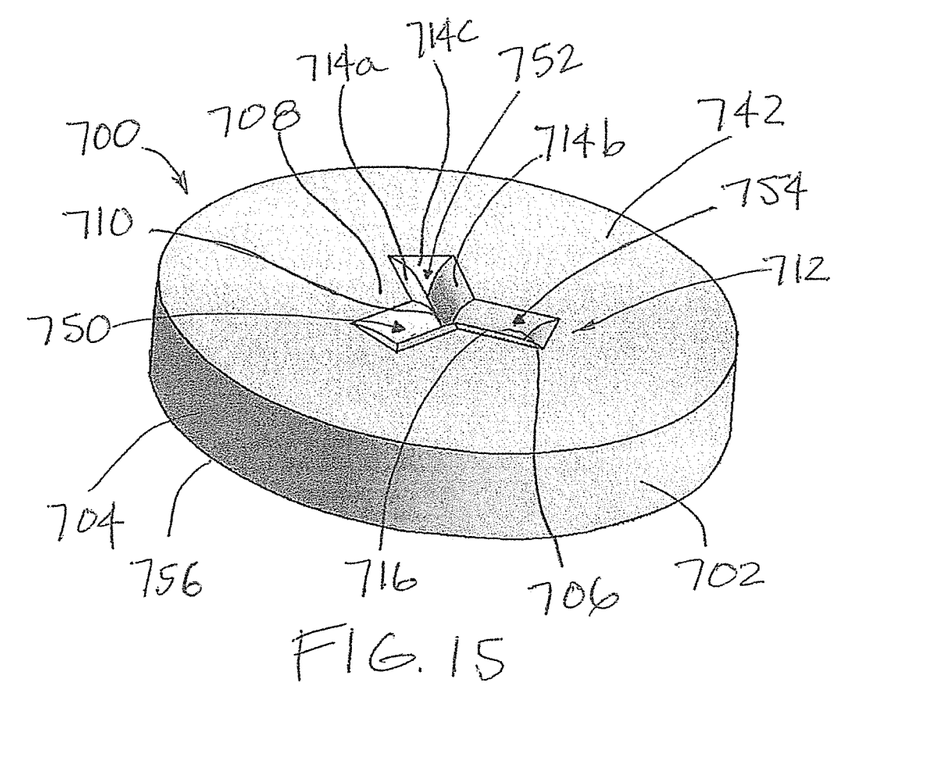
FIG. 15 is a perspective view of a valve disk provided in accordance with further aspects of the present disclosure.

With reference now to FIG. 15, a perspective view of a valve embodiment 700 provided in accordance with further aspects of the present disclosure is shown. The valve 700 comprises a valve body 702 comprising a perimeter 704, a proximal or first surface 742, a distal or second surface 756, and a thickness defined by a gap or distance between the two surfaces. Although perimeter vents are not shown, vents 60 can be incorporated as shown in FIGS. 6 and 7. Centrally, a plurality of slits 706 defining a plurality of flaps 708 are provided. As shown, the valve 700 comprises three slits 706 and three flaps 708. In other examples, fewer than three slits or more than four slits may be provided. The slits preferably meet at a central location 710, which define a through seam extending from the proximal surface 742 to the distal surface 752.

A perspective view of a void 712 is shown formed around the slits 706. The void 712 provides the same advantages discussed above with reference to FIGS. 4a, 4b, 5, 6, 7, and 8. As shown, the void 712 comprises a three-sided or three wings 750, 752, 754 structure with each wing comprising a set of three tapered surfaces 714a, 714b, 714c surrounding each slit 706. The three tapered surfaces include two side tapered surfaces 714a, 714b and one end tapered surface 714c. Generally, the two side surfaces 714a, 714b are longer or larger in surface area than the end tapered surface 714c although it is possible for the reverse to be true. If there are five slits 706, as an example, then five wings would be provided with each wing comprising three tapered surfaces 714a, 714b, 714c. The three tapered surfaces 714a, 714b, 714c can meet along a finite line at the slit 706, similar to the sharp tip 46 of FIG. 4a. Alternatively, the three tapered surfaces 714a, 714b, 714b can terminate at spaced distances so as to form planar surfaces proximate each slit 706, similar to the base surface 314 of FIG. 4b, which has an inner perimeter internally of the void perimeter.

In one example, the valve 700 is formed, such as molded, with the void 712. The slits 706 are then formed by cutting through the valve body 702 at the center of the void. In another example, the void 712 is provided on both the proximal surface and the distal surface. The void 712, like that of FIGS. 4a, 4b, 5, 6, 7, and 8, comprises a perimeter 716 that is recessed or radially inwardly disposed relative to the valve perimeter 704. Thus, the present disclosure is understood to include a valve disc comprising a perimeter, a proximal surface, and a distal surface, and wherein a void is formed centrally of the valve. The present disclosure is further understood to include a perimeter formed around the void and wherein the void perimeter is located radially inwardly of the valve perimeter. The valve can further include a plurality of slits formed at the void. In some examples, a void is formed at the proximal surface and another void at the distal surface. One or more vents may be formed at the valve perimeter. In one example, the one or more vents each comprises a simple cut. In another example, the one or more vents each comprises a notch. In other examples, any of the valves discussed elsewhere herein may incorporate the void 712 with multi-sided wings discussed with reference to FIG. 15.

Although limited embodiments of the valved catheter assemblies and their components have been specifically described and illustrated herein, many modifications and variations will be apparent to those skilled in the art. For example, the various parts of the valve may incorporate alternate materials, etc. Furthermore, it is understood and contemplated that features specifically discussed for one valved catheter assembly embodiment may be adopted for inclusion with another valved catheter assembly embodiment, provided the functions are compatible. For example, reinforcing ribs may be used in another embodiment shown with a void on the proximal surface. Another example is the slits 660 in FIGS. 12, 13 and 14 may be notches as shown in FIG. 7. Accordingly, it is to be understood that the valved catheter assembly assemblies and their components constructed according to principles of the disclosed device, system, and method may be embodied other than as specifically described herein. The disclosure is also defined in the following claims.

What is claimed is:
1. An intravenous (IV) catheter assembly comprising:
 a catheter hub comprising an interior wall surface defining an interior cavity, an opening at a proximal end, and a catheter tube for intravenous use attached thereto and extending from a distal end;

a needle having a needle shaft defining a needle axis projecting distally of an end of a needle hub, said needle projecting through the catheter tube and comprising a needle tip;

a valve sized and shaped to obstruct fluid flow positioned inside the interior cavity of the catheter hub and in contact with the interior wall surface defining the interior cavity, said valve comprising a valve perimeter surrounding a wall surface comprising a thickness, at least one slit having a length and a cut through the thickness of the wall surface and substantially along the length of the at least one slit to define at least two flaps and a void having a void perimeter inwardly positioned relative to the valve perimeter and formed through only part of the thickness of the wall surface, said void comprising at least one wing; and a valve opening device slidingly disposed in the catheter hub to actuate the valve, the valve opening device comprising a nose section having a tapered end for pushing the valve to open the slit of the valve and a plunger end having a plunger element extending proximally of the nose section; the plunger element being sufficiently rigid to transfer a distally directed force to the nose section to push the valve to open the slit;

wherein three tapered surfaces extend from the void perimeter inwardly toward the at least one slit and toward a bottom wall of the void.

2. The catheter assembly of claim 1, further comprising a second slit and a third slit.

3. The catheter assembly of claim 1, wherein the void has a blunt tip or a sharp tip.

4. The catheter assembly of claim 1, wherein the valve further comprises a second void formed through part of the thickness on the wall surface opposite the void.

5. The catheter assembly of claim 1, wherein the valve further comprises a plurality of reinforcing ribs located, at least in part, on the flaps.

6. The catheter assembly of claim 1, further comprising a needle protective device spaced from the needle tip in a ready position and movable relative to the needle tip to a protective position, at least in part, distally of the needle tip to prevent unintended needle sticks.

7. The catheter assembly of claim 1, further comprising a plurality of spaced apart vents cut through the valve perimeter.

8. An intravenous (IV) catheter assembly comprising:
a first hub comprising an interior cavity having a shoulder, a perimeter defining an opening at a proximal end, and a catheter tube for intravenous use having a distal end opening extending distally of the first hub;

a needle having a needle shaft defining a needle axis projecting distally of an end of a second hub, said needle projecting through the catheter tube and comprising a needle tip;

a valve sized and shaped to obstruct fluid flow comprising a valve body comprising a perimeter, said perimeter comprising at least one vent and said valve body comprising at least one inner slit remote from said perimeter; said valve being positioned inside the interior cavity of the first hub;

a valve opening device slidingly disposed in the first hub to actuate the valve, the valve opening device comprising a nose section having a tapered end with an opening structured to push the valve to open the plurality of slits and at least one plunger element extending proximally of the nose section and slidable distally when a male implement projects into the opening of the first hub to transfer a distally directed force to the nose section to push the valve to open the at least one slit; and wherein the valve has at least one void having a void perimeter disposed inwardly of the outer periphery, said void comprising at least one wing comprising three tapered surfaces extending inwardly from the void perimeter toward a bottom wall of the void, surrounding said at least one slit.

9. The catheter assembly of claim 8, comprising a needle guard comprising a proximal wall with an opening sized to obstruct a change in profile on the needle.

10. The catheter assembly of claim 8, wherein the at least one vent is a lengthwise slit.

11. The catheter assembly of claim 8, wherein the at least one vent is a V-shaped notch.

12. The catheter assembly of claim 8, wherein the void has two side tapered surfaces and one tapered end surface.

13. The catheter assembly of claim 8, further comprising a second void positioned opposite the void.

14. The catheter assembly of claim 8, wherein the valve body comprises a cylinder with an open end.

15. The catheter assembly of claim 8, wherein the vent closes when the valve is opened by the valve opening device.

16. The catheter assembly of claim 1, wherein the wall surface is a first wall surface, and wherein the valve comprises a second wall surface comprising at least one slit defining at least two flaps, and a void having a void perimeter inwardly positioned relative to the valve perimeter and formed through only part of the thickness of the wall surface, said void comprising at least one wing comprising a set of tapered surfaces surrounding said at least one slit.

17. The catheter assembly of claim 1, wherein the at least two flaps have interior surfaces and wherein the needle shaft rests against the interior surfaces of the at least two flaps along a through seam.

18. The catheter assembly of claim 1, wherein the at least two flaps have interior surfaces and wherein the needle shaft rests against the interior surfaces so that force vectors at a seam of the at least one slit is perpendicular relative to an axis of the needle shaft.

19. The catheter assembly of claim 1, wherein the valve comprises a hollow cylinder section having a length and a body wall thickness.

20. The assembly of claim 18, further comprising vents running the entire length of the hollow cylinder.

21. The catheter assembly of claim 8, wherein said at least one void is located on a first surface of the valve, and wherein the valve comprises a second wall surface comprising at least one void disposed inwardly of the outer periphery, said void comprising at least one wing comprising three tapered surfaces surrounding said at least one slit.

22. The catheter assembly of claim 8, wherein the at least one slit defines at least two flaps with interior surfaces and wherein the needle shaft rests against the interior surfaces of the at least two flaps along a through seam.

23. The catheter assembly of claim 8, wherein the at least one slit defines at least two flaps with interior surfaces and wherein the needle shaft rests against the interior surfaces so that force vectors at a seam of the at least one slit is perpendicular relative to an axis of the needle shaft.

24. The catheter assembly of claim 8, wherein the valve comprises a hollow cylinder section having a length and a body wall thickness.

25. The assembly of claim 23, further comprising vents running the entire length of the hollow cylinder.

* * * * *